United States Patent
Fein et al.

(10) Patent No.: US 7,381,698 B2
(45) Date of Patent: Jun. 3, 2008

(54) METHODS FOR TREATMENT OF ACUTE PANCREATITIS

(75) Inventors: Seymour H. Fein, New Canaan, CT (US); Edward D. Purich, Silver Spring, MD (US)

(73) Assignee: ChiRhoClin, Inc., Burtonsville, MD (US)

( * ) Notice: Subject to any disclaimer, the term of this patent is extended or adjusted under 35 U.S.C. 154(b) by 0 days.

(21) Appl. No.: 11/007,490

(22) Filed: Dec. 8, 2004

(65) Prior Publication Data

US 2005/0129675 A1 Jun. 16, 2005

Related U.S. Application Data

(60) Provisional application No. 60/529,433, filed on Dec. 12, 2003.

(51) Int. Cl.
*A61K 38/00* (2006.01)
*A61K 38/16* (2006.01)

(52) U.S. Cl. .................. 514/2; 514/8; 514/12

(58) Field of Classification Search ............ None
See application file for complete search history.

(56) References Cited

U.S. PATENT DOCUMENTS

| | | | |
|---|---|---|---|
| 4,443,434 A | | 4/1984 | Lien |
| 4,517,309 A | | 5/1985 | Noda |
| 5,094,837 A | * | 3/1992 | Bis ............... 424/9.34 |
| 6,020,310 A | * | 2/2000 | Beck et al. ............ 514/12 |
| 6,143,306 A | | 11/2000 | Donovan |
| 6,197,746 B1 | | 3/2001 | Beck et al. |
| 6,261,572 B1 | | 7/2001 | Donovan |
| 6,365,593 B2 | | 4/2002 | Rusche et al. |
| 6,498,143 B1 | | 12/2002 | Beck et al. |
| 6,534,063 B1 | | 3/2003 | Fallon |
| 2001/0018049 A1 | | 8/2001 | Sachs et al. |
| 2003/0133906 A1 | | 7/2003 | Deviere et al. |

OTHER PUBLICATIONS

Lightdale et al. Pediatrics. Effects of intravenous secretin on language and behavior of children with autism and gastrointestinal symptoms: a single-blinded, open-label pilot study. 2001; 108(5):1-5.*
Jowell et al. Aliment Pharmacol Ther. A double-blind, randomized, dose response study testing the pharmacological efficacy of synthetic porcine secretin. 2000; 14:1679-1684.*
Keim et al. Hepatogastroenterology. 1985; 32: 91-6.*
FDA document found on FDA website at cder/foi/label/2002/21136s1Ib1.pdf, Secreflo (Trademark) secretin for Injection. NDA 21-136 & NDA 21-206, p. 5-13, published Aug. 29, 2002.*
Manso et al. Peptides. 1989; 10: 255-260.*
Renner et al. J. Clin. Invest. 1983; 72: 1081-1092.*
Zieve L. Gastroenterology. Jan. 1964; 46: 62-7, esp. pp. 62-63.*
Willemer and Adler, Int J Pancreatol. 1991; 9: 21-30.*
"Off-Label" and Investigational Use of Marketed Drugs, Biologics and Medical Devices downloaded on Oct. 18, 2006 from fda.gov/oc/ohrt/irbs/offlabel.html.*
AGA Council: Abstracts Submitted to the AGA, Gastroenterology, vol. 125, No. 2, pp. 605-607 (Aug. 2003).
AGA Council: Abstracts Submitted to the AGA, Gastroenterology, vol. 125, No. 2, pp. 605-607 (Aug. 2003), Printed from the Internet, "Gastroenterology Online", at 5:20 p.m., Oct. 25, 2003.
Tympner, F., et al., "The Treatment of Chronic Recurrent Pancreatitis with Depot Secretin—a Preliminary Report," Hepatogastroenterology, vol. 33, pp. 159-162, 1986.
Renner, I., et al., "Partial Restoration of Pancreatic Function by Exogenous Secretin in Rats with Ceruletide-Induced Acute Pancreatitis," Digestive Diseases and Sciences, vol. 31, No. 3, pp. 305-313, 1986.
Human Secretin Package Label (Apr. 5, 2004).

\* cited by examiner

*Primary Examiner*—Elizabeth C. Kemmerer
*Assistant Examiner*—Christina Borgeest
(74) *Attorney, Agent, or Firm*—Todd E. Garabedian; Wiggin and Dana LLP

(57) ABSTRACT

The invention relates generally to methods for treating acute pancreatitis in patients. The methods comprise administering a therapeutically effective amount of a pharmaceutical composition comprising secretin and a pharmaceutically acceptable carrier.

8 Claims, No Drawings

METHODS FOR TREATMENT OF ACUTE PANCREATITIS

CROSS-REFERENCE TO RELATED APPLICATIONS

This application claims the benefit of U.S. Provisional Application Ser. No. 60/529,433, filed Dec. 12, 2003, which is incorporated by reference herein in its entirety.

BACKGROUND OF THE INVENTION

1. Field of the Invention

The invention relates generally to methods for treating acute pancreatitis in patients. The methods comprise administering a therapeutically effective amount of a pharmaceutical composition comprising secretin and a pharmaceutically acceptable carrier.

2. Brief Description of the Related Art

Acute pancreatitis is an inflammation of the pancreas that occurs when digestive enzymes leak out of the pancreatic ducts and damage the pancreas. The etiology of acute pancreatitis is unknown. It is a syndrome, which may result from multiple factors. The common feature to all cases of acute pancreatitis is a release and activation of digestive enzymes within the exocrine pancreas gland causing inflammation, injury, autolysis and necrosis to the organ. This can also lead to hemorrhage and pseudocyst formation within the gland. Severe upper abdominal pain, nausea and vomiting are the most common symptoms.

Approximately one-third of acute pancreatitis cases are associated with alcohol abuse, one-third with pancreatic cancer and one-third lack concomitant medical conditions and are considered idiopathic. Episodes of acute pancreatitis tend to recur with resulting hospitalizations and morbidity. Many patients develop chronic pancreatitis with ongoing low-grade inflammation of the pancreas, progressive destruction of glandular tissue, anatomical deformities, loss of organ function and digestive capabilities, and chronic pain.

Treatment of acute pancreatitis is medical not surgical and supportive in nature including intravenous fluids, analgesia and sometimes antibiotics.

Secretin is contraindicated in its FDA labeling for use during episodes of acute pancreatitis. This proscription is based on the belief that secretin stimulation of the exocrine pancreas with increased production of water and bicarbonate and greater flow of pancreatic juice containing proteolytic, digestive enzymes through the pancreatic ducts would exacerbate acute pancreatitis and predispose to the formulation of cysts, pseudocysts, and parenchymal necrosis.

Published studies in animal models of the use of secretin with acute pancreatitis are largely negative. Some preliminary studies of experimentally induced acute pancreatitis in rat and mouse models in the early 1980s reported a possible beneficial effect (Renner I G et al., J. Clin. Invest. 72(3): 1081-92, 1983; Niederau C et al., Gasteroenterology 88(5, Pt1):1192-1204 1985; Renner I G et al., Dig. Dis.Sci. 31(3):305-313, 1986). Later, more definitive studies with cerulein-induced and reflux-induced acute pancreatitis models were negative (Keim V et al., Hepatogastroenterology 32(2):91-96, 1985; Infatino A et al., Res. Exp. Med. 190(2): 89-93, 1990), as was a study of secretin for sodium taurocholate-induced acute pancreatitis in rat (Lankisch P G et al., Digestion 26(4):187-191, 1983).

A clinical study from Spain published in 1989 suggested secretin might produce some pain relief in acute pancreatitis (Manso M A et al., Peptides 10(2):255-260, 1989). However, the results of this study were not definitive. The only randomized, double-blind, placebo-controlled trial of secretin for therapeutic use evaluated patients with chronic pancreatitis with acute exacerbations and used a depot formulation of secretin (Tymper F., et al., Hepatogastroenterology 33(4): 159-162, 1986).

Additional examples of treatments for acute pancreatitis in the patent literature include the following:

U.S. Pat. No. 4,443,434 assigned to American Home Products discloses a method for treatment of acute pancreatitis comprising administering an octapeptide in an amount sufficient to inhibit pancreatic enzyme secretion. The octapeptide reduces gastric acid secretion, gastric blood flow and pancreatic enzyme release.

U.S. Published Patent Application No. US2001/0018049 assigned to Allergan Inc., discloses a method of treating a patient suffering from acute pancreatitis by administering an effective amount of a chimeric protein containing an amino acid sequence-specific endopeptidase activity. The chimeric protein ultimately inhibits zymogen release from acinar cells. This results in the reduction or elimination of the autodigestion of pancreatic tissue.

U.S. Pat. No. 6,143,306 assigned to Allergan Sales, Inc., discloses a non-radio therapy therapeutic method of treating disorders of the pancreas such as pancreatitis using a neurotoxin such as botulinum toxin.

U.S. Pat. No. 6,261,572 assigned to Allergan Sales, Inc., discloses a method for treating a pancreatic disorder by local administration of a therapeutic amount of a neurotoxin such as botulinum toxin, into or onto the body of the pancreas in order to treat symptoms of a pancreatic disorder.

U.S. Pat. No. 5,094,837 assigned to Wayne State University discloses a method for using magnetic resonance imaging (MRI) to image the pancreas by using secretin. An amount of secretin is placed in solution and administered to a patient for the purpose of pancreatic imaging. Administration of the secretin is done by IV infusion. The secretin employed in this method can be extracted from porcine or bovine sources or can be genetically recombined porcine, bovine or human secretin.

U.S. Pat. No. 6,020,310 and U.S. Pat. No. 6,498,143, both assigned to Repligen, disclose use of secretin to stimulate pancreatico-biliary fluid secretion in a patient exhibiting autism.

U.S. Pat. No. 6,197,746 assigned to Repligen Corporation discloses methods of using secretin for treating autism.

U.S Pat. No. 6,365,593 assigned to Repligen Corporation discloses methods of diagnosing individuals for autistic disorders, comprising obtaining a sample of urine from the individuals; measuring a level of a methylxanthine in the urine sample; and comparing the level to a normal control or to a threshold level.

U.S. Pat. No. 6,534,063 to Joan Fallon discloses methods of utilizing the fecal chymotrypsin level of an individual as a measure of the success of secretin, other neuropeptides, and peptides or digestive enzyme administration to such individuals, and in particular, as a prognosticative of potential secretin, other neuropeptides, peptides, and digestive enzyme administration for persons having ADD, ADHD, Autism and other PDD related disorders.

None of the treatments currently utilized for acute pancreatitis, have proven to be very effective or have changed the course of the disease. However, the present invention is believed to be an answer to these needs.

SUMMARY OF THE INVENTION

In one aspect, the present invention is directed to a method for treating acute pancreatitis in a patient, comprising the step of administering to a patient a therapeutically effective amount of a pharmaceutical composition comprising secretin and a pharmaceutically acceptable carrier.

This and other aspects will become apparent upon reading the following detailed description of the invention.

DETAILED DESCRIPTION OF THE INVENTION

It has now been unexpectedly found that secretin is effective for treating acute pancreatitis.

In accordance with one embodiment of the method of the present invention, treatment for naturally occurring acute pancreatitis includes administering to a patient in need of such treatment a pharmaceutical composition comprising secretin. Beneficial effects of treating patients suffering from naturally occurring acute pancreatitis include more rapid and/or complete resolution of the episode of pancreatitis, less damage to the pancreatic parenchyma, decreased pain, more rapid resolution of pain, decreased nausea, decreased vomiting, decreased use of analgesics, more rapid time to resumption of oral intake, decreased length of hospitalization, decreased time to resumption of normal daily activities, and decreased time to return to work.

As indicated above, the present invention is directed to administering a therapeutically effective amount of a pharmaceutical composition comprising secretin and a pharmaceutically acceptable carrier. Each of these components are discussed in more detail below.

Secretin is a 3055.5 MW (27 amino acid) gastrointestinal peptide hormone originally extracted from the porcine duodenum. The primary action of secretin is to increase the volume and bicarbonate content of pancreatic juice (Gutierrez L V, et al., Gut 13:721-25 (1972); Laugier R, et al., Digestion 54:54-60 (1993); Cavallini G, et al., Dig. Dis. Sci. 37(1):93-96 (1992)). also increases the pancreatic duct diameter (Glaser J, et al., Int. J. Pancreatol. 15:195-200 (1994); Tulassay Z, et al., Gastroenterol. J. 51:47-50 (1991)) and causes sphincter of Oddi relaxation (Geenen J E et al., Gastroenterology 78:317-24 (1980); Laugier R. Endoscopy 26:222-27 (1994)). Recently, a new synthetic porcine secretin has been developed that has been shown to be equally effective as a pancreatic secretagogue. In the methods of the invention, secretin may be used from any source. Preferably the secretin used in the methods of the present invention is the naturally occurring form, the synthetic form, or the genetically recombined form of porcine, bovine or human secretin. More preferably the secretin is synthetic porcine secretin or synthetic human secretin. One useful form of porcine secretin is manufactured by ChiRhoClin, Inc. (Burtonsville, Md.) and sold under the trade name "SECREFLO" by Repligen Corporation (Waltham, Mass.). Another useful form of porcine secretin is manufactured by ChiRhoClin, Inc. (Burtonsville, Md.) with the tradename "SECREMAX". A useful form of human secretin is manufactured and sold by ChiRhoClin, Inc. under the tradename "SECRETIN-HUMAN".

The secretin may be combined with a pharmaceutically acceptable carrier to form a pharmaceutical composition. Thus, the pharmaceutical compositions of this invention comprise secretin from any source (including pharmaceutically acceptable salts thereof) in combination with any pharmaceutically acceptable carrier, adjuvant or vehicle. Pharmaceutically acceptable carriers, adjuvants and vehicles that may be used in the pharmaceutical compositions of the present invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride (saline), zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of this invention may be administered by any route that produces acceptable bioavailability. Suitable administration methods include, but are not limited to, parenteral methods such as intravenous, subcutaneous and intramuscular and per os (by mouth), or sublingual, and transdermal bolus or continuous infusions of secretin may be used.

The compounds of the invention are preferably administered internally, e.g., intravenously, in the form of conventional pharmaceutical preparations, for example in conventional enteral or parenteral pharmaceutically acceptable excipients containing organic and/or inorganic inert carriers, such as water, gelatin, lactose, starch, magnesium stearate, talc, plant oils, gums, alcohol, VASELINE (petroleum jelly), or the like. The pharmaceutical preparations can be in conventional solid forms, for example, tablets, dragées, suppositories, capsules, or the like, or conventional liquid forms, such as suspensions, emulsions, or the like. If desired, they can be sterilized and/or contain conventional pharmaceutical adjuvants, such as preservatives, stabilizing agents, wetting agents, emulsifying agents, buffers, or salts used for the adjustment of osmotic pressure. The pharmaceutical preparations may also contain other therapeutically active materials.

The pharmaceutical preparation of the invention should include an amount of secretin effective for preventing acute pancreatitis. The effective dosage will depend on several factors, including body weight, body mass index, age, gender and disease severity. Suitable dosages may be, for example, in the range of about 2 to 50 micrograms secretin, more preferably of about 8 to about 36 micrograms secretin, and most preferably between 15 and 20 micrograms secretin per dose. In addition, multiple doses of secretin may be required to be administered each day over a period of time (for example, a dose of 16 micrograms secretin (approximately 0.2 micrograms per kilogram body weight) intravenously, four times per day for 7 days.

EXAMPLES

The invention is further described by the following Examples, but is not intended to be limited by the Examples. All parts and percentages are by weight and all temperatures are in degrees Celsius unless explicitly stated otherwise.

A. Treatment of Acute Pancreatitis

There are several possible mechanisms by which secretin might exert a therapeutically beneficial effect on the course and/or signs and symptoms of acute pancreatitis. While not wishing to be bound by any particular theory, it is believed that secretin stimulates the release from the exocrine pancreas parenchyma of a large volume of water, bicarbonate and potentially harmful digestive enzymes, which can cause pancreatic inflammation. This effect may also dilute the proteolytic and other digestive enzymes produced by the exocrine pancreas causing them to be less irritating. In addition, by increasing exocrine pancreas secretion, secretin may flush the pancreatic ducts removing activated enzymes from the gland. Secretin, by relaxing the Sphincter of Oddi and causing the papilla to open, may reduce the resistance to the flow of pancreatic juice out of the gland and into the duodenum. This might decrease intraductal pressure and speed the transit of pancreatic juice through the ducts and out of the gland.

The pharmaceutical compositions of this invention may be administered by any route that produces acceptable bioavailability. As defined herein, acceptable bioavailability refers to any amount of secretin that produces a beneficial effect to treat any form of pancreatitis. Suitable administration methods include but are not limited to parenteral methods such as intravenous, subcutaneous and intramuscular and per os (by mouth) or sublingual and transdermal bolus or continuous infusions of secretin may be used.

Suitable dose regimens of secretin to treat acute pancreatitis may be, for example, in the range of about 2 to 480 micrograms per day intravenously, subcutaneously or intramuscularly in divided doses from 3 to 6 times per day. A continuous infuision of secretin achieving a cumulative daily dose in this range may also be used. Oral, sublingual and transdermal doses would be higher based on relative bioavailability to intravenous administration. More preferably a daily parenteral dose of about 24 to about 160 micrograms of secretin, and most preferably of about 48 to about 128 micrograms of secretin would be used.

Secretin would be administered as soon after diagnosis of acute pancreatitis as possible and given daily (in divided doses or continuous infusion) for about 3 days to about 14 days.

Efficacy Evaluation

Pancreatitis is the most common medically significant complication following Endoscopic Retrograde Cholangio-Pancreatography (EROP) procedures. The symptoms and pathophysiology of post-ERCP pancreatitis and acute pancreatitis are identical, and patients at risk for postERCP pancreatitis or suffering early signs of the condition provide good data for evaluation of therapies for acute pancreatitis. An evaluation of the clinical efficacy of dosages of secretin to treat or prevent the onset of pancreatitis in patients undergoing ERCP is described below.

A total of 979 ERCP patients were randomized, received study drug and were evaluable for efficacy. The demographic profiles of the patients who were randomized and received treatment with study drug by treatment group are summarized in Table 1.

TABLE 1

Demographic Characteristics

| | Treatment Group | | |
|---|---|---|---|
| Parameter | SPS | Placebo | p-value |
| Age (years) | N = 488 | N = 491 | |
| Mean (SD) | 55.6 (16.3) | 55.8 (17.0) | 0.8650 |
| Range (min-max) | 17.0-93.0 | 18.0-91.0 | |
| Weight (kg) | N = 488 | N = 491 | |
| Mean (SD) | 76.4 (20.5) | 76.8 (23.2) | 0.7734 |
| Range (min-max) | 36.0-208.0 | 36.0-241.0 | |
| Height (cm) | N = 488 | N = 491 | |
| Mean (SD) | 167.9 (15.0) | 168.3 (13.2) | 0.6356 |

TABLE 1-continued

Demographic Characteristics

| | Treatment Group | | |
|---|---|---|---|
| Parameter | SPS | Placebo | p-value |
| Range (min-max) | 59.0-198.0 | 16.0-200.0 | |
| Gender (%) | N = 488 | N = 491 | |
| Male (%) | 225 (46.11) | 203 (41.34) | 0.1387 |
| Female (%) | 263 (53.29) | 288 (58.66) | |
| Race (%) | N = 486 | N = 490 | |
| Caucasian | 396 (81.48) | 395 (80.61) | 0.7986 |
| African-American | 81 (16.67) | 88 (17.96) | |
| Hispanic | 2 (0.41) | 1 (0.20) | |
| American Indian | 4 (0.82) | 5 (1.02) | |
| Asian | 3 (0.62) | 1 (0.20) | |
| Tobacco Use (%) | N = 482 | N = 487 | |
| Yes | 154 (31.98) | 127 (26.08) | 0.0475 |
| No | 328 (68.05) | 360 (73.92) | |
| Alcohol Use (%) | N = 481 | N = 483 | |
| Yes | 112 (23.28) | 119 (24.64) | 0.6510 |
| No | 369 (76.72) | 364 (75.36) | |
| History of Post-ERCP Pancreatitis | N = 442 | N = 490 | |
| Yes (%) | 26 (5.88) | 22 (5.00) | 0.6566 |
| No (%) | 416 (94.12) | 418 (95.00) | |

Statistical Method = Chi-Square

The two treatment groups were similar in all demographic characteristics. The only marginally significant difference was in the frequency of tobacco use by medical history, which was more common in the group treated with sPS (p=0.0475). There were slightly more males and fewer females in the sPS group, but this was not a statistically significant difference. Overall, the two treatment groups were well matched demographically.

During an ERCP, a variety of diagnostic and therapeutic procedures may be performed by the endoscopist depending on the medical purposes of the ERCP, the medical condition of the patient and the observations made during the ERCP. A comparison of the frequency of these procedures between the two treatment groups appears in Table 2.

TABLE 2

Incidence of Intra-ERCP Procedures

| | Treatment Group | | |
|---|---|---|---|
| Procedure | SPS (N = 488) | Placebo (N = 491) | p-value |
| Cannulation CBD (%) | | | |
| Yes | 361 (73.98) | 368 (74.95) | 0.7695 |
| No | 127 (26.02) | 123 (25.08) | |
| Cannulation of Pancreatic Duct (%) | | | |
| Yes | 220 (45.08) | 219 (44.60) | 0.8978 |
| No | 268 (54.92) | 272 (55.40) | |
| Sphincterotomy of CBD (%) | | | |
| Yes | 140 (28.69) | 159 (32.38) | 0.2125 |
| No | 348 (71.31) | 332 (67.62) | |
| Sphincterotomy of Pancreatic Duct (%) | | | |
| Yes | 26 (5.34) | 30 (6.11) | 0.6802 |
| No | 461 (94.66) | 461 (93.89) | |
| Stent Removal from CBD (%) | | | |
| Yes | 58 (11.93) | 59 (12.02) | 1.0000 |

TABLE 2-continued

Incidence of Intra-ERCP Procedures

| | Treatment Group | | |
|---|---|---|---|
| Procedure | SPS (N = 488) | Placebo (N = 491) | p-value |
| No Stent Removal from Pancreatic Duct (%) | 428 (88.07) | 432 (87.98) | |
| Yes | 17 (3.56) | 17 (3.46) | 1.0000 |
| No | 469 (96.50) | 474 (96.54) | |
| Stent Insertion into CBD (%) | | | |
| Yes | 108 (22.22) | 116 (23.67) | 0.6480 |
| No | 378 (77.78) | 375 (76.37) | |
| Stent Insertion into Pancreatic Duct (%) | | | |
| Yes | 23 (4.73) | 42 (8.55) | 0.0203* |
| No | 463 (95.27) | 449 (91.45) | |
| Stone Extraction (Basket) from CBD (%) | | | |
| Yes | 35 (7.20) | 48 (9.78) | 0.1687 |
| No | 451 (92.80) | 443 (90.22) | |
| Stone Extraction (Balloon) from CBD (%) | | | |
| Yes | 55 (11.32) | 70 (14.26) | 0.1806 |
| No | 431 (88.68) | 421 (85.74) | |
| Manometry of CBD (%) | | | |
| Yes | 19 (3.91) | 17 (3.46) | 0.7370 |
| No | 467 (96.09) | 474 (96.54) | |
| Manometry of Pancreatic Duct (%) | | | |
| Yes | 11 (2.26) | 7 (1.43) | 0.3526 |
| No | 475 (97.74) | 484 (98.57) | |

*Chi-Square Test

The two groups were well matched with regard to the types and incidences of various intra-ERCP procedures performed. The only statistically significant difference was in the frequency of stent insertion into the pancreatic duct (42 cases in the placebo group vs. 23 cases in the sPS group). As described in more detail below, the incidence of post-ERCP pancreatitis in the sPS group was actually slightly higher (5/23=21.7%) than in the placebo group (8/42=19%). Only 3 additional cases of post-ERCP pancreatitis occurred in the placebo group vs. the sPS group in this patient population.

The primary efficacy variable was the overall incidence of post-ERCP pancreatitis. The results are depicted in Table 3.

TABLE 3

Overall Incidence of Post-ERCP Pancreatitis

| | Treatment Group | | |
|---|---|---|---|
| Parameter | SPS (N = 488) | Placebo (N = 491) | p-value |
| Incidence of Post-ERCP Pancreatitis | | | |
| Yes (%) | 44 (9.02) | 69 (14.05) | 0.0161* |
| No (%) | 444 (90.98) | 422 (85.95) | |

*Fisher Exact Test

The difference in the incidence of post-ERCP pancreatitis between the two treatment groups in favor of the sPS treated patients was highly significant. The p-value of 0.0161 was sufficient to allow the study to be discontinued on the basis of the planned interim analysis of approximately 1,000 evaluable patients. The severity of the cases of post-ERCP pancreatitis, which did occur in each treatment group is depicted in Table 4 below.

TABLE 4

Post-ERCP Pancreatitis Severity

| | Treatment Group | | | |
|---|---|---|---|---|
| Severity Rating (%) | SPS (N = 488/44) | Placebo (N = 491/69) | p-value | Overall |
| Minimal | 13 (29.55) | 19 (27.54) | 0.289 | 0.6278 |
| Mild | 14 (31.82) | 17 (24.64) | 0.590 | |
| Moderate | 9 (20.45) | 17 (24.64) | 0.117 | |
| Severe | 1 (2.27) | 2 (2.90) | — | |
| Unknown | 7 (15.91) | 14 (20.28) | — | |
| Total | 44 (100.0) | 69 (100.0) | | |

As shown in Table 4, there was no obvious difference or shift in the spectrum of severity 15 of post-ERCP pancreatitis between the two groups. While sPS treated patients had significantly fewer cases of pancreatitis, secretin did not seem to exert an obvious temporizing effect on the cases, which did occur relative to placebo. There were many cases of unknown severity, and it is possible there was a modest effect in terms of reducing severity, which was not visible because of the missing severity data.

The frequency of post-ERCP pancreatitis was evaluated in numerous patient sub-populations defined by the types of procedures performed during the ERCP. These results are described in Table 5.

TABLE 5

Incidence of Post-ERCP Pancreatitis in Patient Sub-Populations

| | Treatment Group | | |
|---|---|---|---|
| Procedure Related Sub-Populations | SPS | Placebo | p-value |
| Cannulation of CBD | N = 361 | N = 368 | |
| Yes (%) | 27 (7.48) | 56 (15.22) | 0.0010* |
| No (%) | 334 (92.52) | 312 (84.78) | |
| Cannulation of Pancreatic Duct | N = 220 | N = 219 | |
| Yes (%) | 30 (13.64) | 42 (19.18) | 0.1237 |
| No (%) | 190 (86.36) | 177 (80.82) | |
| Sphincterotomy of CBD | N = 140 | N = 159 | |
| Yes (%) | 7 (5.00) | 33 (20.75) | 0.0001* |
| No (%) | 133 (95.00) | 126 (79.25) | |
| Sphincterotomy of Pancreatic Duct | N = 26 | N = 30 | |
| Yes (%) | 12 (46.15) | 8 (14.29) | 0.1666 |
| No (%) | 14 (57.85) | 22 (73.33) | |
| Stent Removal from CBD | N = 58 | N = 59 | |
| Yes (%) | 1 (1.72) | 3 (5.08) | 0.6185 |
| No (%) | 57 (98.28) | 56 (94.92) | |
| Stent Removal from Pancreatic Duct | N = 17 | N = 17 | |
| Yes (%) | 2 (11.76) | 1 (5.88) | 1.0000 |
| No (%) | 15 (88.24) | 16 (94.12) | |
| Stent Insertion into CBD | N = 108 | N = 116 | |
| Yes (%) | 3 (2.78) | 10 (8.62) | 0.0856 |
| No (%) | 105 (97.22) | 106 (91.38) | |
| Stent Insertion into Pancreatic Duct | N = 23 | N = 42 | |
| Yes (%) | 5 (21.74) | 8 (19.05) | 1.0000 |
| No (%) | 18 (78.26) | 34 (80.95) | |
| Stone Extraction (Basket) | N = 35 | N = 48 | |
| Yes (%) | 1 (2.86) | 6 (12.50) | 0.2298 |
| No (%) | 34 (97.14) | 42 (87.50) | |
| Stone Extraction (Balloon) | N = 55 | N = 70 | |

TABLE 5-continued

Incidence of Post-ERCP Pancreatitis in Patient Sub-Populations

| | Treatment Group | | |
|---|---|---|---|
| Procedure Related Sub-Populations | SPS | Placebo | p-value |
| Yes (%) | 4 (7.27) | 6 (8.57) | 1.0000 |
| No (%) | 51 (92.73) | 64 (91.43) | |
| Manometry of CBD | N = 19 | N = 17 | |
| Yes (%) | 4 (21.05) | 9 (52.94) | 0.0819 |
| No (%) | 15 (78.95) | 8 (47.06) | |
| Manometry of Pancreatic Duct | N = 11 | N = 7 | |
| Yes (%) | 5 (45.45) | 5 (76.43) | 0.3665 |
| No (%) | 6 (54.58) | 2 (28.57) | |

*Fisher Exact Test

This analysis indicates that the intra-ERCP procedures most associated with the risk of developing post-ERCP pancreatitis are cannulation of the CBD, cannulation of the pancreatic duct and sphincterotomy of the CBD. There is the suggestion that sphincterotomy of the pancreatic duct, stent insertion into the pancreatic duct and manometry of both the CBD and pancreatic duct may also be associated with a higher increase of post-ERCP pancreatitis but the sample size was too small to be conclusive.

Further evaluation of the intra-ERCP procedures with meaningful sample sizes, which are associated with a higher risk of post-ERCP pancreatitis, i.e. cannulation of the CBD, and pancreatic duct, and sphincterotomy of the CBD demonstrates a highly significant protective effect of sPS. For cannulation of the CBD, the p-value=0.0010 and for sphincterotomy of the CBD, p<0.0001. For cannulation of the pancreatic duct, the p-value did not reach statistical significance (p=0.1237) but there was a numerical trend in favor of a preventive effect for sPS. Stent insertion into the CBD also showed a strong numerical trend in favor of sPS exerting a protective effect (3/108=2.78% for sPS vs. 10/116=8.62% for placebo) with the p-value of 0.0856 narrowly missing statistical significance. Manometry of the CBD almost demonstrates a statistically significant effect in favor of sPS (4/19 =21.05%) vs. placebo (9/17=52.94%) with a p-value of 0.0819. The sample size, however, was small.

Additional secondary efficacy analyses were performed on post-ERCP pain, nausea, and vomiting using a 0 to 10 digital scale. There were no significant differences between the treatment groups for baseline (pre procedure) pain, nausea and vomiting. There were also no significant differences in these variables post-ERCP although there was a slight numerical trend indicating less nausea for sPS (p=0.0284).

Analysis of the differences between pre and post-ERCP pain, nausea and vomiting showed statistically significant increases for both treatment groups for each variable. The mean increases, however, were numerically smaller for the sPS group for each of the three variables and achieved statistical significance for nausea. These results are shown in Table 6.

TABLE 6

Pain, Nausea, Vomiting

| | Treatment Group | | |
|---|---|---|---|
| Parameter (Mean) | SPS | Placebo | p-value |
| Pain Pre-ERCP | 1.4 (0.6) (N = 483) | 1.4 (0.6) (N = 487) | 0.0668* |
| (SD) | | | |
| Pain Post-ERCP | 1.8 (3.0) (N = 485) | 2.2 (3.3) (N = 487) | |
| (SD) | | | |
| Change in Pain (SD) | 0.4 (3.4) (N = 480) | 0.8 (7.3) (N = 483) | |
| Nausea Pre-ERCP | 0.6 (1.7) (N = 483) | 0.6 (1.8) (N = 487) | 0.0284* |
| (SD) | | | |
| Nausea post-ERCP | 0.9 (2.1) (N = 485) | 1.3 (2.4) (N = 487) | |
| (SD) | | | |
| Change in Nausea | 0.3 (2.5) (N = 480) | 0.7 (2.6) (N = 483) | |
| (SD) | | | |
| Vomiting pre-ERCP | 0.1 (0.8) (N = 482) | 0.1 (0.5) (N = 486) | 0.0776* |
| (SD) | | | |
| Vomiting post-ERCP (SD) | 0.6 (1.9) (N = 485) | 0.8 (2.1) (N = 487) | |
| Change in Vomiting (SD) | 0.5 (2.0) (N = 479) | 0.7 (2.1) (N = 482) | |

*Fisher Exact Test

The symptoms and signs associated with pancreatitis (pain, nausea and vomiting), were identical in scored severity pre-ERCP but in each case showed much less of an increase post-ERCP in the sPS group. These between group differences in change reached significance for nausea and narrowly missed significance for pain and vomiting.

Additional secondary efficacy variables assessed were return to baseline (pre-ERCP levels of activity) and the time in days to return of pre-ERCP activity levels. There was a small difference in the percentage of patients reporting return to baseline activity within the follow-up period (2 to 4 days post-ERCP) favoring the placebo group (p=0.0230) (49.78% vs. 42.09%). Interims of the mean number of days required to achieve pre-ERCP activity levels, was 0.6 (±1.0) for the sPS group and 0.7 (±0.9) for the placebo group. An attempt was made to obtain information on return to work. Relatively few data points were able to be collected, however, because a large percentage of patients were not working pre-ERCP (retired, too ill, etc.) among the 185 patients (95 in the sPS group and 90 in the placebo group) providing relevant responses for this variable, 46.32% of sPS patients and 50.00% of placebo patients reported returning to work within the follow-up period. These results were not significant.

The results of this large, randomized, double-blind, placebo controlled study demonstrates a highly statistically significant protective effect for sPS in terms of preventing post-ERCP pancreatitis, i.e. decreasing the incidence relative to placebo. This finding applied to the overall study population and to several patient sub-populations defined by the intra-ERCP procedures performed. The effectiveness if sPS in decreasing the occurrence of post-ERCP pancreatitis was most evident in the sub-groups who underwent cannulation of the CBD and sphincterotomy of the CBD, but also seen in patients who underwent cannulation of the pancreatic duct, stent insertion into the CBD and management of the CBD.

Many patients who develop post-ERCP pancreatitis have a prior history of episodes of acute pancreatitis, and some of these patients have the onset of symptoms of acute pancreatitis just prior to having the ERCP procedure. Apart from its association with ERCPs, acute pancreatitis may be caused by alcohol ingestion, tumors, or gallstones blocking the common bile duct and pancreatic duct, hyperlipidemia, and for idiopathic reasons. The data described above show secretin to be effective in decreasing the incidence of acute pancreatitis following the ERCP procedure, and suggest that secretin would be effective in treating the early stages of acute pancreatitis so it does not clinically progress to a more advanced stage with more serious clinical signs and symptoms.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entireties.

What is claimed is:

1. A method for treating acute pancreatitis in a human patient, comprising the step of administering to a human patient suffering from acute pancreatitis a therapeutically effective amount of a pharmaceutical composition comprising secretin and a pharmaceutically acceptable carrier, said pharmaceutical composition capable of treating said acute pancreatitis in said human patient, and wherein the amount of secretin administered to said patient in said pharmaceutical composition ranges from 2 to 480 micrograms per day.

2. The method of claim 1, wherein the amount of secretin administered to said patient in said pharmaceutical composition ranges from 24 to 160 micrograms per day.

3. The method of claim 2, wherein the amount of secretin administered to said patient in said pharmaceutical composition ranges from 48 to 128 micrograms per day.

4. The method of claim 1, wherein said secretin is a naturally occurring form of secretin.

5. The method of claim 1, wherein said secretin is a synthetic form of secretin.

6. The method of claim 5, wherein said synthetic form of secretin is synthetic porcine secretin.

7. The method of claim 1, wherein said secretin is a genetically recombined form of porcine, bovine, or human secretin.

8. The method of claim 1, wherein said pharmaceutically acceptable carrier is selected from the group consisting of ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride (saline), zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat, and combinations thereof.

* * * * *